United States Patent [19]
Berk et al.

[11] Patent Number: 6,000,535
[45] Date of Patent: Dec. 14, 1999

[54] DISPOSABLE MIXING WELLS

[75] Inventors: Kenneth J. Berk, Newton; Frederick M. Berk, Brookline; Donald Berk, Newton, all of Mass.

[73] Assignee: Pulpdent Corporation

[21] Appl. No.: 09/025,172

[22] Filed: Feb. 18, 1998

[51] Int. Cl.[6] ................................................. A61B 19/02
[52] U.S. Cl. .................... 206/63.5; 206/369; 206/820; 220/23.4
[58] Field of Search .................... 206/63.5, 438, 206/363–370, 562–564, 820; 220/23.4, 23.6, 23.8; 264/46.8; 366/602; 433/79, 77, 49, 163

[56] References Cited

U.S. PATENT DOCUMENTS

| | | | |
|---|---|---|---|
| 3,016,134 | 1/1962 | Borsuk | 206/63.5 |
| 4,203,515 | 5/1980 | Kahn et al. | 206/63.5 |
| 5,106,297 | 4/1992 | Discko, Jr. | 206/63.5 |
| 5,377,823 | 1/1995 | Steen et al. | 206/63.5 |
| 5,749,730 | 5/1998 | Johnsen et al. | 206/63.5 |
| 5,752,598 | 5/1998 | Zdarsky | 206/369 |
| 5,762,192 | 6/1998 | Jacobs et al. | 206/63.5 |

*Primary Examiner*—Paul T. Sewell
*Assistant Examiner*—Luan K. Bui
*Attorney, Agent, or Firm*—Lee & Hollander

[57] ABSTRACT

An article of manufacture and a method of making same wherein a plurality of mixing wells is formed as a unitary sheet of individual mixing wells arranged in rows and columns. The boundary between each mixing well is scored, perforated, or otherwise made to allow individual pieces to be removed from the sheet. Preferably, the mixing wells may be pressure formed rather than being vacuum formed.

12 Claims, 2 Drawing Sheets

DISPOSABLE MIXING WELLS

FIELD OF THE INVENTION

This invention is related to plastic molded mixing wells and in particular to a method of manufacturing such mixing wells in sheets of multiple wells.

BACKGROUND OF THE INVENTION

Many dental procedures require that small amounts of materials be mixed or held for use on a patient. Examples of these materials include composites, bonding agents, etchants, and other materials. Typically, these materials will be mixed or held in a small container and then applied to a patient with a brush or other tool, during which the mixing well will become contaminated. Thus, mixing wells must be cleaned or disposed of after use.

Small, plastic, disposable mixing wells have become popular with dentists and others having similar requirements. Typically these mixing wells are injection molded or otherwise formed from plastic sheets and consist of one or more mixing cavities supported by a base. The dimensions are typically on the order of two to four centimeters on a side up to twelve centimeters on a side. When formed in this manner, the individual mixing wells are small and light weight and are difficult to handle and store both during the manufacturing and packaging stage and also during storage and use by a dentist or other end user.

SUMMARY OF THE INVENTION

The present invention includes a method of manufacturing disposable mixing wells to provide a sheet comprising multiple mixing wells. In the invention, a plurality of mixing wells is formed as a sheet of individual mixing wells arranged in rows and columns. The boundary between each mixing well is scored, perforated, or otherwise made to allow individual pieces to be removed from the sheet. Further, the mixing wells may be pressure formed rather than being vacuum formed. Making and providing the mixing wells in this form has many advantages over other methods of making and providing the wells individually or in other forms.

DESCRIPTION OF THE DRAWINGS

The advantages and operation of the present invention are more fully described in the following description of the preferred embodiment and by reference to the drawings, of which.

DESCRIPTION OF THE PREFERRED EMBODIMENT

Figures 1, 2:
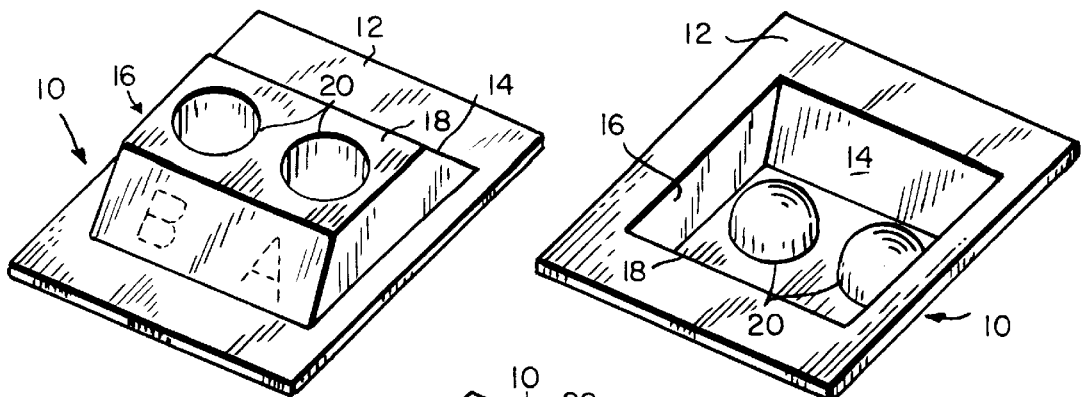
FIGS. 1 and 2 are top and bottom views of a typical mixing well.

FIGS. 1 and 2 are top and bottom views respectively of a typical disposable mixing well 10. The mixing well 10 includes a flat base portion 12, typically of square or rectangular shape and two to four centimeters on each side. A raised center section 14 extends upwardly from the base 12. In the embodiment shown in FIGS. 1 and 2, the raised center section is trapezoidal in cross-section with end walls 16 perpendicular to the plane of base 12.

The top surface 18 of the raised center section 14 has one or more cavities 20 formed therein to provide the actual depressions or cavities in which materials are placed. In the described embodiment, two mixing cavities are provided which are generally hemispherical in shape, however it should be appreciated that other shapes may be utilized and the number of wells may be varied. It is generally preferable to have the bottom of the well cavity 20 be rounded in shape to aid in achieving complete mixing. Optional markings such as letters 17 may be molded into the raised section 14. It is to be understood that the term mixing well refers to the unitary structure 10 which may include one or more cavities 20 in which the holding of materials or the mixing operation is actually performed. The described trapezoidal shape for the raised center section 14 aids in providing structural rigidity to the relatively thin plastic material from which it is formed. Other shapes may be used for the center section 14.

As shown in FIGS. 1 and 2, the mixing well 10 is formed from a sheet of plastic material into the configuration shown and described. The material of mixing well 10 is preferably a high molecular weight polyolefin, although other materials may be utilized, including polyethylene, polypropylene, or other plastics. In the preferred embodiment, the thickness of the plastic after forming is approximately 0.020 inches.

Figure 3:
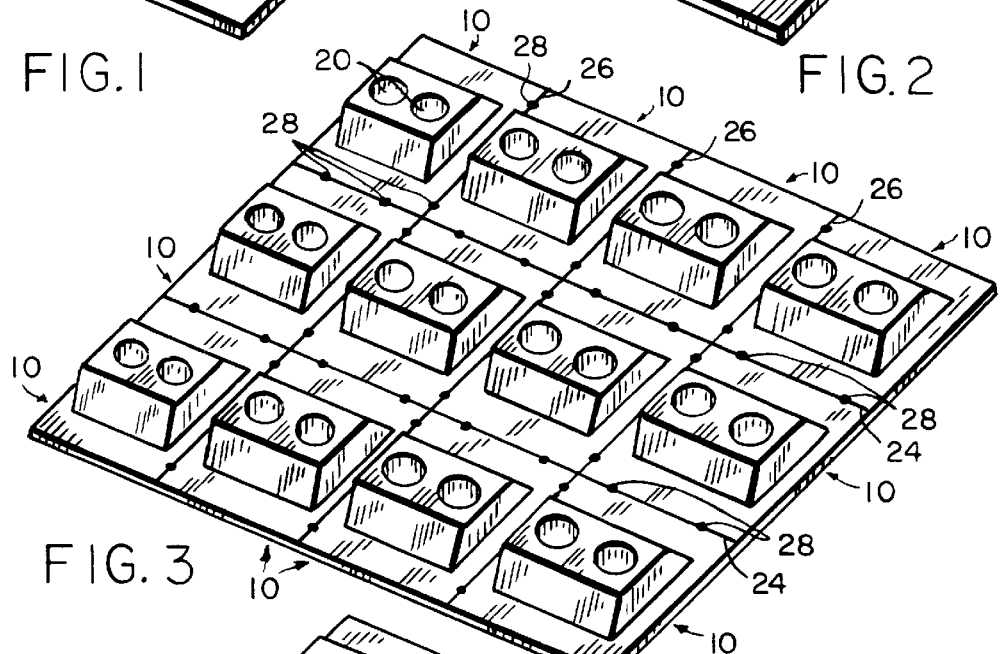
FIG. 3 is a view of a sheet of mixing wells made in accordance with the invention.

While the disposable mixing well shown in FIGS. 1 and 2 works well, it is very small, and accordingly there are problems with handling, packing, and storing the individual wells. Typically, disposable mixing wells of this type are packaged together with dental materials in kits. The present invention manufactures individual disposable mixing wells in a different manner than heretofore practiced. In the present invention, a plurality of individual wells 10 are formed from a single sheet of plastic 22. The individual wells 10 are laid out in a plurality of rows and columns. In the illustration of FIG. 3, the sheet has three rows, each row having four individual wells, but other arrangements can, of course, be used.

The boundaries between the individual wells is denoted in FIG. 3 by lines 24 marking the division between rows, and lines 26 marking the division between columns. The boundary lines 24 and 26 show the location of separation means which normally connects the individual mixing wells 10, but which allows individual wells to be separated from one another by the manual application of moderate force.

The separation means may be formed in various ways. In the preferred embodiment, the separation means is formed after the step of forming the plurality of wells 10 on sheet 22 by scoring row and column boundaries 24 and 26 by means of a cutting die. Various patterns may be used to achieve the desired objective of allowing selected portions of sheet 22 to be removed. In the preferred embodiment, the scoring die is formed so that the individual mixing wells 10 are completely separated along the boundary lines 24 and 26 except for two locations along each boundary separating a adjacent mixing wells. Such a pattern is illustrated in FIG. 3 where dots 28 designate the connections between adjacent mixing wells 10, the remaining portions of the boundaries 24 and 26 being completely cut through by the cutting die. It has additionally proved beneficial to configure the cutting die so that the attachment points 28 are reduced in thickness to approximately a third of the original thickness of the sheet, thereby reducing the strength of attachment points 28. This method may be used with a single connection between adjacent mixing wells, although two connections are preferred. An alternate scoring pattern does not completely separate the individual wells anywhere along boundaries, but merely scores the boundaries 24 and 26 to reduce the thickness and strength of the plastic material along the entire length of the boundaries. Other patterns of openings and perforations may be used.

Figure 4:
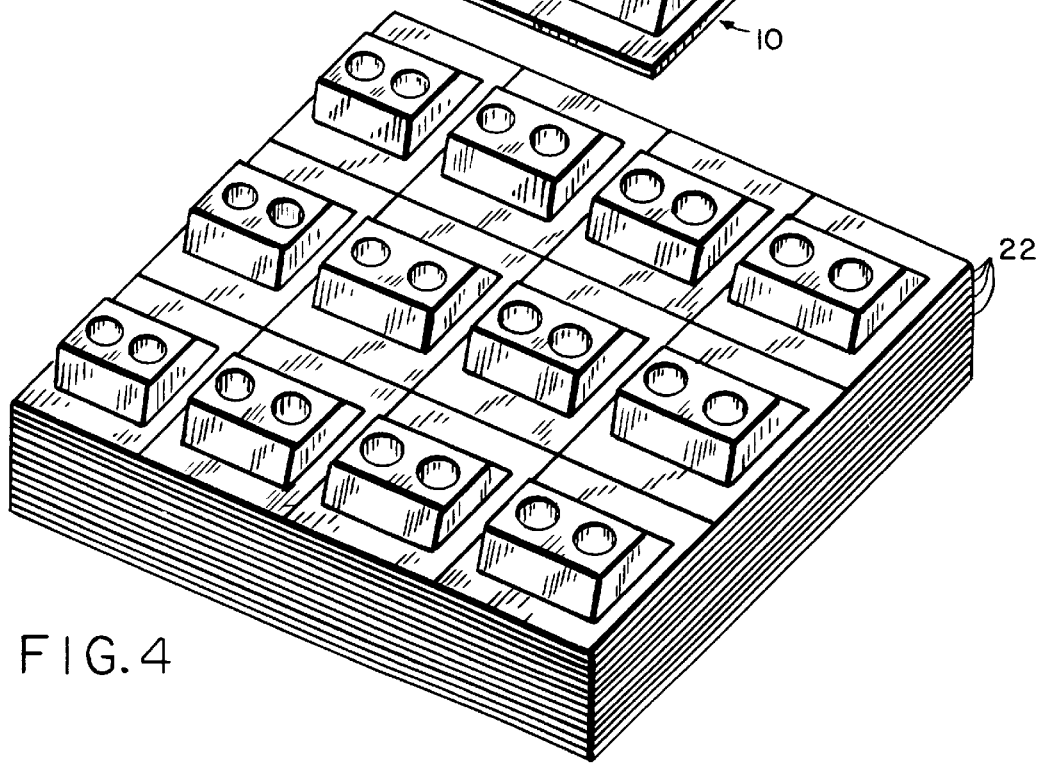
FIG. 4 shows a stack of sheets of mixing wells.

When formed as shown and described above, sheets of multiple mixing wells may be easily stacked, as shown in FIG. 4 where a plurality of sheets 22 as shown in FIG. 3 are stacked on top of each other. As shown in FIG. 4, when multiple sheets 22 are stacked, the raised center sections 14 of individual mixing wells in a sheet fit inside of or nest in the center section 14 of the well directly above, so that the flat base portions 12 of the wells in adjacent sheets lie on top of one another. This provides a very compact configuration for the stacked sheets 22 and additionally allows a block of mixing wells to be torn off and separated from the stack, as described below. It can be seen that large numbers of individual mixing wells 10 may be conveniently and stably boxed when so stacked. When packaging is done by hand, this markedly improves the speed and ease of packaging large numbers of the mixing wells. When packaged by machine, fewer operations are required, and less complex machinery is needed to load a box with a predetermined number of wells.

A user may select a single sheet from such a stack in mass storage and by this means conveniently take a small number of mixing wells to a location where they will be used. Additionally, such a sheet will tend to be easier to find and less prone to upset and possible contamination when stored in the typical drawer or cabinet with other similarly small items.

Figure 5:
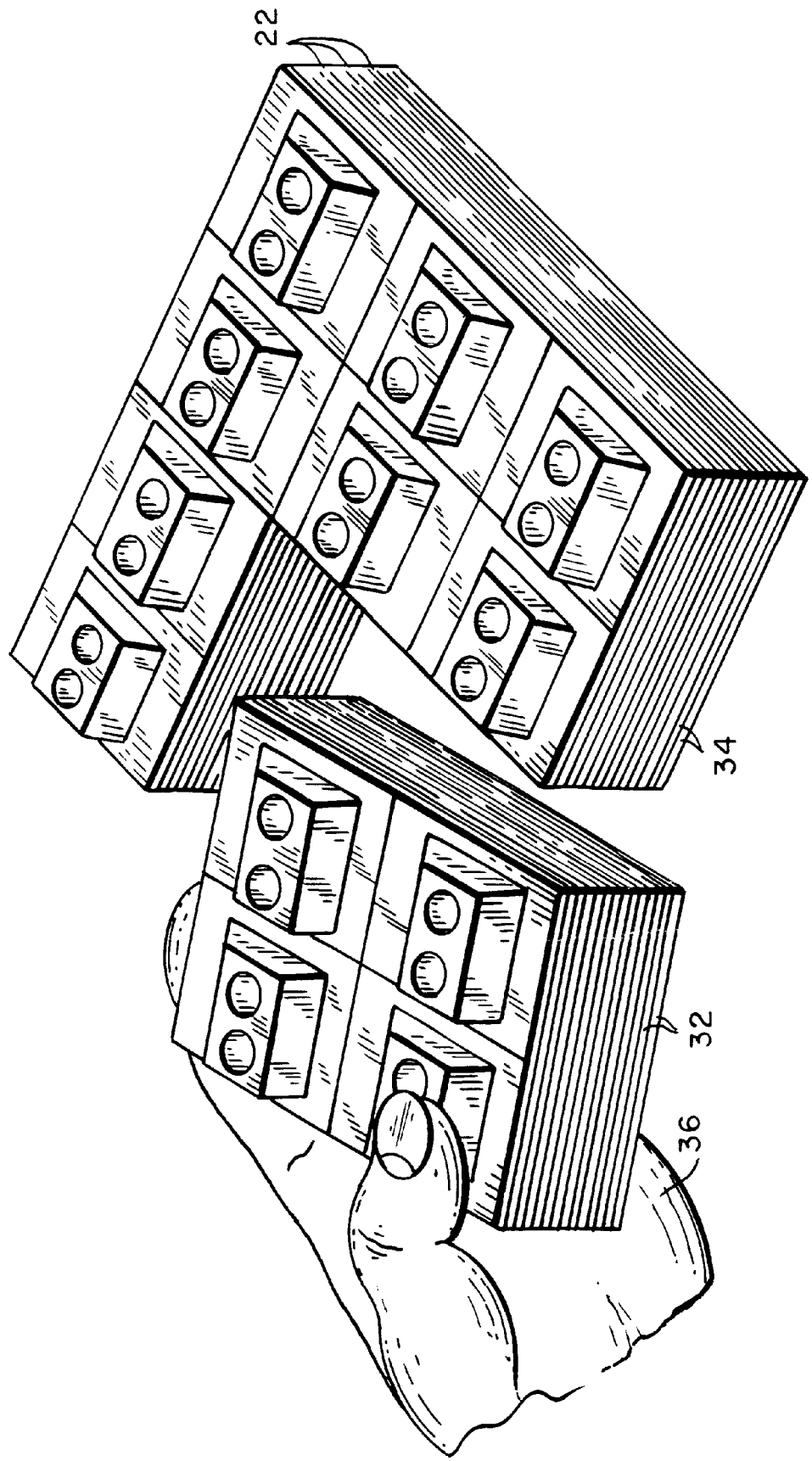
FIG. 5 illustrates the ease with which a block of wells can be broken off of a stack of sheets.

If a configuration of smaller area than an entire sheet is desired, the present invention allows a user to separate a sheet into smaller sections or to separate a stack of sheets into a smaller size block than the complete stack of sheets. FIG. 5 illustrates the ease with which a small block 32 may be manually removed from a stacked set of sheets 22, if such a configuration is desired.

The wells may be formed by vacuum forming or pressure forming. Vacuum forming tends to cause the well cavity to thin out and frequently results in undesirable pinholes at the bottom of the well where the thinned out material is broken by the vacuum suction. To avoid this problem, a modified mold may be used which has a vent formed in a ring around a solid means in the center of the cavity mold, but this approach may produce a ring formation at the well bottom. The preferred forming method, which eliminates these problems, is pressure forming, wherein pressure from air or an assist die from above reduces the amount of vacuum required to form the well cavities so that the cavity bottoms are well-rounded without pinholes or rings.

There has been described a new and useful method for making mixing wells in sheet form having a plurality of separable mixing well structures. While the operation and advantages of the invention have been described with reference to the exemplary embodiments described above, it should be appreciated that modifications to these embodiments will be made by those of ordinary skill in the art in applying the teachings of the invention to different situations and applications. Accordingly, the present invention should not be limited by the embodiments described above, but rather the scope of the invention should be interpreted in accordance with the following claims.

What is claimed is:

1. A method of manufacturing mixing wells, including the steps of:

forming in a sheet of a plastic material a plurality of individual wells arranged in rows and columns, adjacent rows and columns being separated from neighboring rows and columns by boundaries, including the steps of:

forming for each well a raised center portion which extends upwardly from a flat base portion surrounding the center portion and which is adapted to support a mixing cavity; and forming in each raised center portion at least one mixing cavity closed on the bottom, open on the top, extending downwardly into the center portion, and having a rounded bottom;

the steps of forming the raised center portions and forming the cavities including the step of forming the center portion and cavities in a shape that allows individual mixing wells to nest when vertically stacked one on top of another with the raised center portion of individual mixing wells extending substantially into the raised center portion of the mixing well above so that the flat base portions of adjacent sheets lie on top of one another, thereby to allow for closely stacking a plurality of said sheets containing rows and columns of mixing wells; and scoring the sheet along the boundaries between each of the rows and between each of the columns to provide regions of reduced strength along the boundaries so that a plurality of mixing wells less that the total number of wells formed in the sheet may be removed by separating individual wells along the scored boundaries.

2. The method of claim 1 wherein the step of scoring includes the step of cutting through the plastic sheet along each row and column boundary between adjacent mixing wells for a majority of each boundary while leaving at least one connection uncut connecting each mixing well to each adjacent mixing well.

3. The method of claim 2 including the additional step of scoring each of said uncut connections to reduce the thickness of the connection.

4. The method of claim 1 including the step of leaving two connections uncut between each mixing well and adjacent mixing wells.

5. The method of claim 4 wherein the step of forming a plurality of individual wells includes the step of pressure forming said raised center portions and said downwardly extending cavities.

6. The method of claim 1 wherein the step of scoring includes the step of reducing the thickness of the plastic sheet along the length of each boundary without cutting completely through the sheet.

7. A sheet of a plurality of mixing wells comprising:

a plurality of individual mixing wells arranged in rows and columns, adjacent rows and columns being separated by boundaries therebetween, each individual mixing well including:

a flat base portion adapted to support the mixing well;

a raised center portion extending upwardly from the base portion;

at least one mixing cavity formed in the raised center portion, the cavity being open on the top and closed on the bottom and having a rounded bottom surface;

the flat base portions and mixing cavities being shaped to allow individual mixing wells to nest when vertically stacked one on top of another with the raised center portion of individual mixing wells extending substantially into the raised center portion of the mixing well above so that the flat base portions of adjacent sheets line on top of one another, thereby to allow for closely stacking a plurality of said sheets containing rows and columns of mixing wells; and separation means extending along the boundaries between the rows and columns for reducing the force required to tear off one or more individual mixing wells from the sheet of mixing wells.

8. A sheet of mixing wells as set forth in claim 7 wherein the sheet of mixing wells is formed from a polyolefin plastic.

9. A sheet of mixing wells as set forth in claim 7 wherein the separation means includes a scoring along said boundaries wherein part of the boundary between each adjacent mixing well and each of its neighbors is cut completely through with at least one uncut connection being left between adjacent mixing wells.

10. A sheet of mixing wells as set forth in claim 9 wherein the separation means includes two uncut connections between adjacent mixing wells.

11. A sheet of mixing wells as set forth in claim 9 wherein the flat base portions of each mixing well are of substantially uniform thickness and wherein the uncut connections are reduced in thickness with respect to the thickness of the base portions.

12. A sheet of mixing wells as set forth in claim 7 wherein the flat base portions of each mixing well are of substantially uniform thickness and wherein the separation means includes a reduction in thickness, relative to the thickness of the base portions, extending along the entire length of said row and column boundaries.

* * * * *